(12) United States Patent
Nycz et al.

(10) Patent No.: US 7,474,223 B2
(45) Date of Patent: Jan. 6, 2009

(54) METHOD AND APPARATUS FOR IMPLANT IDENTIFICATION

(75) Inventors: Jeffrey H. Nycz, Collierville, TN (US); Steven M. Tethrake, Collierville, TN (US); Mark Pelo, Macy, IN (US); Robert Varner, Germantown, TN (US); Paul Elliott, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 346 days.

(21) Appl. No.: 11/108,130

(22) Filed: Apr. 18, 2005

(65) Prior Publication Data

US 2006/0232408 A1 Oct. 19, 2006

(51) Int. Cl.
A61B 5/05 (2006.01)
G08B 13/14 (2006.01)

(52) U.S. Cl. .................... 340/572.8; 606/424

(58) Field of Classification Search ... 340/568.1–572.9; 600/424, 431, 325, 327, 332, 339, 423; 606/86 R–105.5; 623/16.11, 23.63; 128/843
See application file for complete search history.

(56) References Cited

U.S. PATENT DOCUMENTS

| | | | |
|---|---|---|---|
| 4,075,632 A | 2/1978 | Baldwin et al. |
| 4,360,801 A | 11/1982 | Duhame |
| 4,390,880 A | 6/1983 | Henoch |
| 4,739,328 A | 4/1988 | Koelle et al. |
| 5,030,807 A | 7/1991 | Landt et al. |
| 5,557,280 A | 9/1996 | Marsh et al. |
| 5,858,020 A | 1/1999 | Johnson et al. |
| 5,910,172 A | 6/1999 | Penenberg |
| 5,963,132 A | 10/1999 | Yoakum |
| 6,013,104 A | 1/2000 | Kampner |
| 6,447,448 B1 | 9/2002 | Ishikawa et al. |
| 6,749,639 B2 | 6/2004 | Lewallen |
| 2004/0008123 A1 | 1/2004 | Carrender et al. |
| 2004/0267297 A1 | 12/2004 | Malackowski |
| 2005/0012617 A1* | 1/2005 | DiSilvestro et al. ...... 340/572.8 |

(Continued)

FOREIGN PATENT DOCUMENTS

WO WO 96/39099 12/1996

(Continued)

OTHER PUBLICATIONS

International Search Report mailed Aug. 23, 2006 from European Patent Office.

(Continued)

Primary Examiner—George A Bugg
Assistant Examiner—Jennifer Mehmood
(74) Attorney, Agent, or Firm—Medtronic Spinal and Biologics

(57) ABSTRACT

A method and apparatus for automatically identifying surgical implants by use of a radio-frequency tag (RFID) is disclosed. The method, apparatus, and system enable a radio-frequency tagged implant to receive an interrogation signal from a reader and to respond to the interrogation signal with identifying information about the tagged implants. The interrogation signal interrogates the implant to ascertain its information, and the RFID tag affixed on the implant in turn transmits a signal back to the reader. The method, apparatus, and system can track, inspect, and verify surgical implants, to assess, for example, any wear and tear on implants, and/or positional displacement of components of the implant.

31 Claims, 6 Drawing Sheets

U.S. PATENT DOCUMENTS

| | | | |
|---|---|---|---|
| 2005/0247319 A1* | 11/2005 | Berger | 128/898 |
| 2006/0047283 A1* | 3/2006 | Evans et al. | 606/102 |
| 2006/0056128 A1* | 3/2006 | Cranford et al. | 361/207 |
| 2006/0143439 A1* | 6/2006 | Arumugam et al. | 713/153 |
| 2006/0173291 A1* | 8/2006 | Glossop | 600/424 |
| 2006/0232412 A1* | 10/2006 | Tabacman et al. | 340/572.1 |

FOREIGN PATENT DOCUMENTS

| | | |
|---|---|---|
| WO | WO 01/35872 A1 | 5/2001 |
| WO | WO 2005/046467 A | 5/2005 |

OTHER PUBLICATIONS

Use of Radio Frequency Devices, National ID Program (Cattle & Deer) A Discussion Paper, Dec. 2001, Animal Health Board.

Falcon, Carl, Inside Implantable Devices, Medical Design Technology, Oct. 2004.

* cited by examiner

US 7,474,223 B2

METHOD AND APPARATUS FOR IMPLANT IDENTIFICATION

FIELD OF THE INVENTION

The embodiments generally relates to a method and apparatus for implementing radio frequency identification techniques, and more specifically to a method and apparatus for identifying surgical implants.

DESCRIPTION OF RELATED ART

Hips and knees receive continuous stress from walking, running, sporting activity, or injury and are more commonly affected by the wearing of cartilage (degenerative arthritis) than the hand joints. A wide range of metals and their alloys, polymers, ceramics and composites are used in surgically implanting medical devices and prostheses. Most implanted devices are constructed of more than one kind of material (implants of complex composition). Metal alloys have been developed for these applications to provide improved physical and chemical properties, such as strength, durability and corrosion resistance. Major classes of metals used in medical devices include stainless steels, cobalt-chromium alloys and titanium (as alloys and unalloyed). In addition, metal-on-polyethylene implants are common in hip and knee replacements, among other replacement parts. But wear affects some of those implants, and regardless whether the wear is related to the material the orthopedic implant is made of, or the surgical technique used to implant it into a subject, there is a need to acquire information regarding the type, age, and current condition of the implant.

Joint replacement surgery involves replacing a destroyed joint with an artificial joint. In knee or hip replacement surgery, the artificial joint is made out of metal and plastic. In the case of joint replacement in the hand, the new joint is most commonly composed of silicone rubber or the subject's own tissues such as a portion of tendon.

Joint replacement surgery, also known as arthroplasty, is very common. Each year, orthopedic surgeons perform thousands of joint replacement surgeries in the U.S.—the majority of these procedures is on the large weight bearing joints such as the hips and knees. Joint replacement surgery in the hand is typically used in treating severe arthritis that involves the small joints of the hand. These orthopedic replacements, just like the natural orthopedic parts they replaced, are under daily and repeated stresses, developing wear and tear, thereby requiring examination on a timely basis. In order for orthopedic surgeons to ascertain whether such parts have undergone severe wear and tear, or are about to fail, the subject is interviewed in regard to how he/she feels, then the joint is x-rayed to ascertain the level of wear and tear.

Tracking and managing orthopedic implant replacements is an important health issue, and its effectiveness is paramount to the hundreds of thousands of individuals that currently have such replacements implanted in them, as well as the many who will receive orthopedic implants in the future. Such orthopedic replacements normally are implanted in a subject (i.e. a human being, animal or the like) as a replacement to a natural bone or in some instances, fusing bones together, thereby enabling subjects who receive those implants to function normally. The basics of prosthetic implants can be found in, for example, U.S. Pat. Nos. 5,858,020, 5,910,172, 6,013,104, and 6,749,639, the disclosures of which are incorporated herein by reference in their entirety. Over time, these implants, which normally are made of materials such as metals and their alloys, polymers, ceramics, and composites, undergo certain wear and tear, and in certain instances fail due to an imperfect operation.

Currently there are no methods or equipment that exists today that allow one to safely and quickly ascertain the condition of orthopedic implants without the use of x-rays, or magnetic resonance imaging bulky machines that are placed in specialized rooms in hospitals. Another problem that hampers the usage of those machines is the health issue, in regard to a patient being subjected to multiple sessions of radiation through the x-ray and/or MRI exposure. Therefore, there is a need in the art of orthopedic, and other surgical implants for a more robust, less expensive, and safer procedure for collecting information about those implants.

RFID tags can include either passive or active devices. Active devices are self-powered by a battery, for example. Passive devices do not contain a discrete power source, but derive their energy from an RF signal used to interrogate the RFID tag. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, the RFID tag can permit new or additional information to be stored in the RFID tag's memory, or can permit the RFID tag to manipulate data or perform some additional functions.

Data carriers such as memory devices provide an alternative method for tracking and providing information about items. Memory devices permit linking large amounts of data with an object or item. Memory devices typically include a memory and logic in the form of an integrated circuit ("IC") and a mechanism for transmitting data to and/or from the device. For example, a radio frequency identification ("RFID") tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are incorporated herein by reference in their entirety. RFID tags generally are formed on a substrate and can include, for example, analog RF circuits and digital logic and memory circuits. The RFID tags also can include a number of discrete components, such as capacitors, transistors, and diodes. The RF transmission of data can be accomplished with modulated back scatter as well as modulation of an active RF transmitter.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE EMBODIMENTS

In accordance with a feature of an embodiment of the invention, there is provided a method for obtaining information concerning a surgical implant that includes presenting a subject having one or more RFID-tagged surgical implants into a radio frequency field of a reader device, transmitting an interrogation signal from the reader device, receiving the interrogation signal by the one or more radio frequency tagged surgical instruments, transmitting back to the reader device, an RF signal containing data including at least positional data from the radio frequency tags of the one or more surgical implants, and comparing the positional data received from the radio frequency tags of the one or more surgical implants to a database.

In accordance with another feature of an embodiment of the invention, there is provided a method for obtaining information concerning an implant that includes acquiring positional information about at least one RFID-tagged screw affixed to a surgical implant in a subject, placing the subject in proximity to an RF reader, acquiring current positional information of the RFID-tagged implant, and comparing the current positional information of the RFID-tagged implant to data in a database.

Another feature of an embodiment of the invention includes an apparatus for obtaining information concerning the contents of an implant that includes one or more surgical implants tagged with one or more radio frequency identification tags prior to inserting into a subject, a reader device capable of transmitting a signal to and receiving a signal from the one or more radio frequency identification tags a in a wireless radio frequency field, a database connected to the reader device for storing information about the one or more surgical implants, and a data decoder that compares data received by the reader device from the radio frequency identification tags of the one or more surgical implants to the database.

Yet another feature of an embodiment includes an apparatus for obtaining information concerning the position of an orthopedic implant that includes one or more RFID-tagged screws positioned in one or more implants, a calculator for acquiring positional information of the RFID-tagged implant, a memory for storing positional information of the one or more RFID-tagged implants, an RF reader placed in proximity to the one, or more tagged implants for acquiring current positional data, and a data decoder for comparing the current positional information of the RFID-tagged implant to data in the memory.

Other aspects and advantages of the invention will become apparent from the following detailed description, taken in conjunction with the accompanying drawings, illustrating by way of example the principles of the invention.

BRIEF DESCRIPITION OF THE DRAWINGS

Purposes and advantages of embodiments of the present invention will be apparent to those of ordinary skill in the art from the following detailed description in conjunction with the appended drawings in which like reference characters are used to indicate like elements, and in which.

DETAILED DESCRIPTION OF THE PREFERRED EMBODIMENTS

Figure 1:
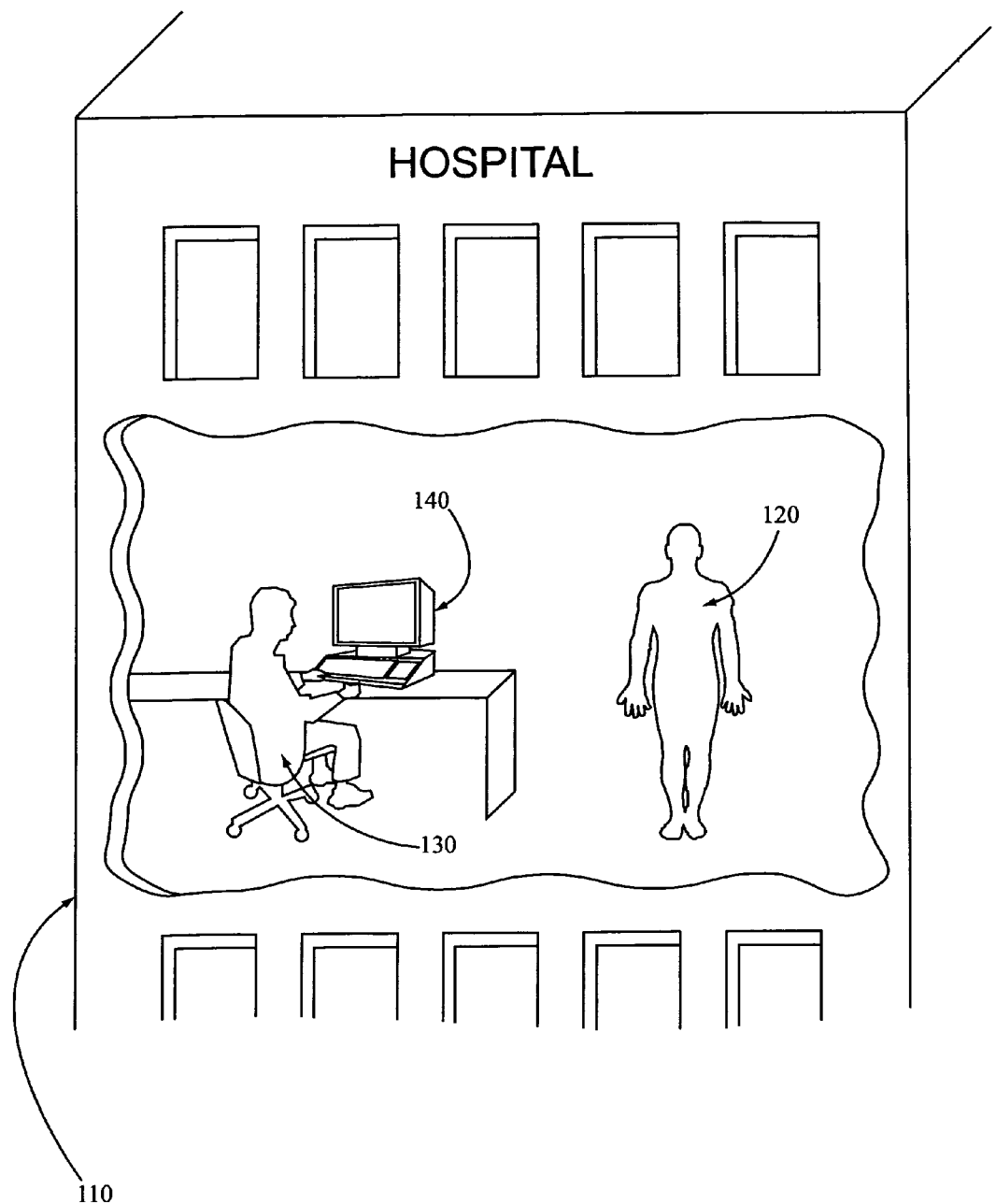
FIG. 1 is a schematic diagram of a hospital visit by a subject according to an embodiment of the invention.

The following description is intended to convey a thorough understanding of the embodiments described herein by providing specific embodiments and details involving automating and adding value to medical and surgical implants, and implant kits. It is understood, however, that the invention is not limited to these specific embodiments and details, which are exemplary only. It further is understood that one possessing ordinary skill in the art, in light of known systems and methods, would appreciate the use of the invention for its intended purposes and benefits in any number of alternative embodiments, depending upon specific design and other needs.

Features of certain embodiments of the invention provide a method and apparatus for automatically and wirelessly inventorying orthopedic implants and the like, by retrieving information from the implant. The information may preferably include tracking information indicative of the manufacturer, part number, serial number and manufacturing lot history, usage and age of each implant, as well as shelf life. Other information may constitute, developing a pedigree for the history of the implant for purposes of authorization for use, including assurances that the RFID-tagged implant was never implanted before The method and apparatus provides for lower costs in collecting information of surgical orthopedic implants, increases the accurate verification of how the implant is performing, and permits a real-time data collection resulting in fast data acquisition that speeds up the diagnosis of subjects with orthopedic implants.

Features of embodiments of the invention also are capable of circumventing some of the costs associated with using x-ray to acquire information from orthopedic implants by implementing radio frequency tagging of each orthopedic implant, and creating a database on a wireless reader in order to wirelessly compare and ascertain the history of each tagged orthopedic implant as patients arrive at a hospital or a doctor's office. One advantage of using RFID is that it obviates the use of cumbersome implant detection apparatus such as X-ray, and MRI (Magnetic Resonance Imaging) machines that typically are stored in special rooms, and manned by specialized technicians. An RFID system preferably includes three components: (i) an antenna; (ii) a transceiver (often the antenna and transceiver are combined into one reader); and (iii) a transponder (the RF tag) electronically programmed with certain unique information. The antenna emits radio frequency waves to activate the transponder (tag) in order to read or write data to it. In turn, the tag transmits data back to the antenna, and the data can be used to interface with a database to carry out a function such as an analysis of the condition of the orthopedic implant.

A feature of an embodiment of the invention provides a method and apparatus for automatically and wirelessly ascertaining orthopedic implant conditions and the like. The method and apparatus preferably retrieves information from a radio frequency tag affixed to an orthopedic implant. The information may include, but is not limited to, information regarding who manufactured the implant, part and serial number (if any), manufacturing data, date of the implant, and the place where operation occurred. The method and apparatus reduces the time and expense associated with accurately acquiring vital information in relation to orthopedic implants, increases accurate verification of data pertaining to each orthopedic implant with a reduction of specialized human contact, and also provides real-time data collection resulting in fast data acquisition, which ultimately speeds up diagnosis and repair of those orthopedic implants.

According to a feature of an embodiment of the invention, a subject with an orthopedic implant is positioned proximate to an RFID reader. The orthopedic implant includes one or more radio frequency identification tags (RFID Tags) that were affixed thereto prior to the initial surgery where the orthopedic implant was inserted into the subject. Alternatively, the RFID tags could be affixed to the implant after surgery, or to an existing implant during a subsequent surgery. It is preferred, though not required, that the tags identify each orthopedic implant in terms of one or more of the following: its manufacturer; part and serial number (if any); manufacturing data, date of the surgical implant; the place where the operation took place; historical data, such as the name of the clinic where the surgical implant was done and the doctor(s) who performed the operation. Other information maybe included as well.

A method according to one embodiment of the invention includes presenting a subject with such an orthopedic implant into a wireless radio frequency field of a reader device that emits a low frequency RF signal, activating an RFID tag, and enabling a response by the tag via a transceiver/antenna combination. The transceivers along with the antenna, collect data from the RFID tag and passes the data in a wireless fashion to a wireless reader to determine actions needed to be taken such as replacing the orthopedic implant.

Another embodiment provides a method, apparatus, and system for identifying orthopedic implant(s) inserted in a subject as a replacement for a natural orthopedic part, wherein the orthopedic implant has been previously radio frequency tagged. At a later time and date, incoming subjects may arrive at a hospital, a clinic or a doctor's office for evaluation and possible repair or replacement of the implant depending on the its condition. A typical system of this embodiment includes, but is not limited to, an RFID-tagged orthopedic implant, any or a combination of a desk-top personal computer(s), lap-top computer(s), personal digital assistant(s), and/or sub-notebook that are prevalent at clinics. Various combinations of these items may be included in the system, and not all items need be present. These items may comprise a wireless fidelity (WIFI) local Area Network that implements a peer-to-peer network, thereby allowing all the wireless equipment in the hospital, clinic or doctor's office to communicate with each other without the need for a gateway or an access point. In another embodiment, the reader items may comprise sensors of a mesh network that employ micro-electro-mechanical systems (MEMS).

One aspect of this embodiment provides a method whereby: (i) a subject with an RFID-tagged orthopedic implant, such RFID tags using a frequency determined by the Federal Communications Commission (FCC), which is available for medical implant communications, and preferably in the range of 402 MHz to a maximum of 405 MHz, arrives at a hospital, a clinic or a doctor's office; (ii) a portable RFID reader/writer, or a handheld RFID scanner transmits an interrogation signal; (iii) in response to the interrogation signal, a transceiver/antenna combination that is incorporated into the RFID tag of the tagged orthopedic implant, transmits a data signal using backscatter modulation; (iv) the tagged orthopedic implant transfers the data to the reader; and (v) the data is compared to information maintained in a local database pertaining to the history of each individual orthopedic implant.

Embodiments of the invention now will be explained with reference to the figures. In FIG. 1, a typical subject 120, with one or more RFID-tagged orthopedic or other implants is illustrated in accordance with one feature of an embodiment of the invention. The subject 120 who has received an RFID-tagged implant during an earlier operation arrives at a hospital, clinic or doctor's office 110 to be examined by a doctor 130, using, for example, any form of computing apparatus 140. Typically, the subject's surgical implant is tagged with a frequency determined by the Federal Communications Commission (FCC), which is available for medical implant communications, and preferably in the range of about 402 MHz to about 405 MHz, frequencies that have propagation characteristics conducive to the transmission of radio signals within the human body.

The RFID tag preferably is attached to one or more portions of the implant that are susceptible to wear and tear, such as screws inserted to fuse a bone or bones together, one or more screws inserted in a surgical implant (e.g., plate, rod) to hold it together, or a knee joint, hip, shoulder, or other replacement prostheses. Typically, the medical or surgical implants are radio frequency tagged with passive RFID tags to enable the identity and condition of each implant to be remotely and accurately inspected and verified without resorting to cumbersome techniques that exploit nuclear radiation, such as X-ray, CT scan, MRI or PET scan. The RFID tags also enable determination of certain information about the implant and its implantation, including, for example, date, place, responsible doctor, and repair (if any). Any other data important or relevant to surgical implants also may be encoded into the RFID tag, as will be appreciated by those skilled in the art. Because the RFID tag(s) preferably are passive, an alternating current created by the received carrier signal of the reader supplies power to the tags. The information stored in the tag(s) is transmitted back to the reader using backscatter modulation.

Embodiments of the invention are useful for patients ready to receive a surgical implant, or that already have an implant. In either case the implant will have affixed thereto at least one RFID tag, either prior to implantation, or during a subsequent surgical procedure should the implant already be present in the subject. Either prior to or during the surgical procedure in which the tagged implant is implanted (or the implant is tagged), information regarding the implant is stored in memory on the RFID tag, and positional and other relevant information concerning the implant is stored in a database. In one preferred embodiment, two tags are present on the implant, or an implant includes two screws, each having an RFID tag affixed thereto. The tags themselves may store, and a database also may store positional information regarding the relative positions of the respective tags. The database can be accessed at a later time to acquire the original information, or the original information can be acquired by retrieving it from the tag's memory. This will enable subsequent comparison of the original or initial information with later acquired information. In a particularly preferred embodiment, a comparison can be made between the current and original relative positions of the respective tags to see if the implant, or screws, have become displaced or worn.

Figure 2:
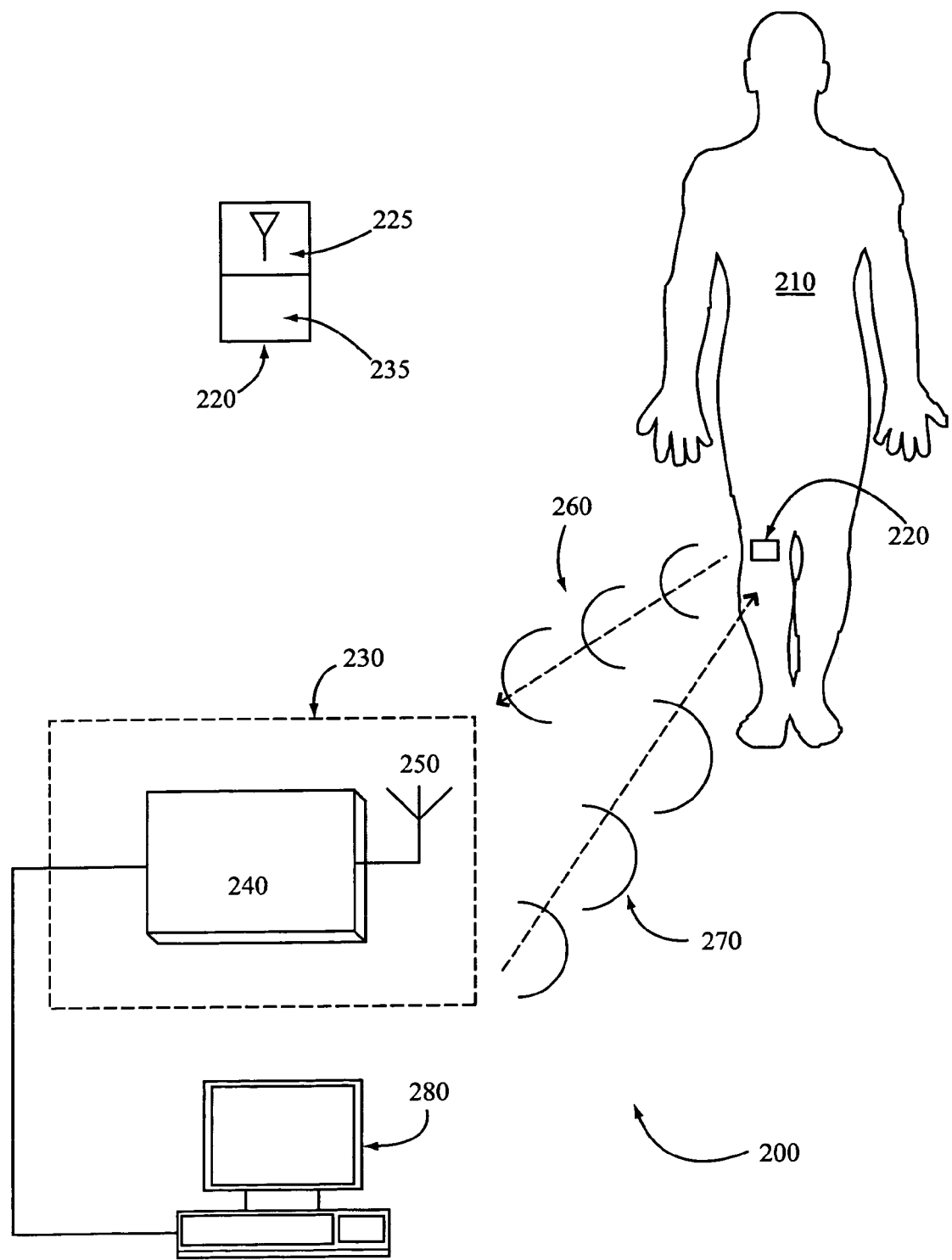
FIG. 2 is a schematic diagram of a subject with an RFID tagged implant and a wireless reader with a database according to an embodiment of the invention.

According to another feature of an embodiment of the invention, (FIG. 2), a subject 210, who optionally may have one or more of an orthopedic or other RFID tagged implants may arrive at a hospital, clinic or doctor's office. As the subject 210 arrives for a check-up, the subject is presented into a wireless radio frequency field 270 from a reader device 230, that receives a data signal 260 back from the RFID tag(s). The reader device 230 may be comprised of a wired or wireless equipment, such as a hand-held scanner, PDA, hand-held computer with a flash card, a fixed station, or any other reader that is capable of receiving a data signal 260, and/or a device that is capable of emitting an RF signal 270. The reader 230, preferably comprised of a transceiver 240 along with the antenna 250, collects data from the RFID tagged implants and passes the data to a database 280, in a wired fashion as shown in FIG. 2, or in a wireless fashion to one or more units that may be one or more of a desk-top personal computer(s), lap-top computer(s), personal digital assistant(s), and/or sub-notebook. The information received from the RFID tag then maybe compared to information created about the implant(s) prior to and during the implant operation, and to determine whether actions need to be taken. The various actions that may be taken include removing and replacing the implant, doing minor re-alignment, or any other action deemed necessary for the health of the subject.

Figure 3:
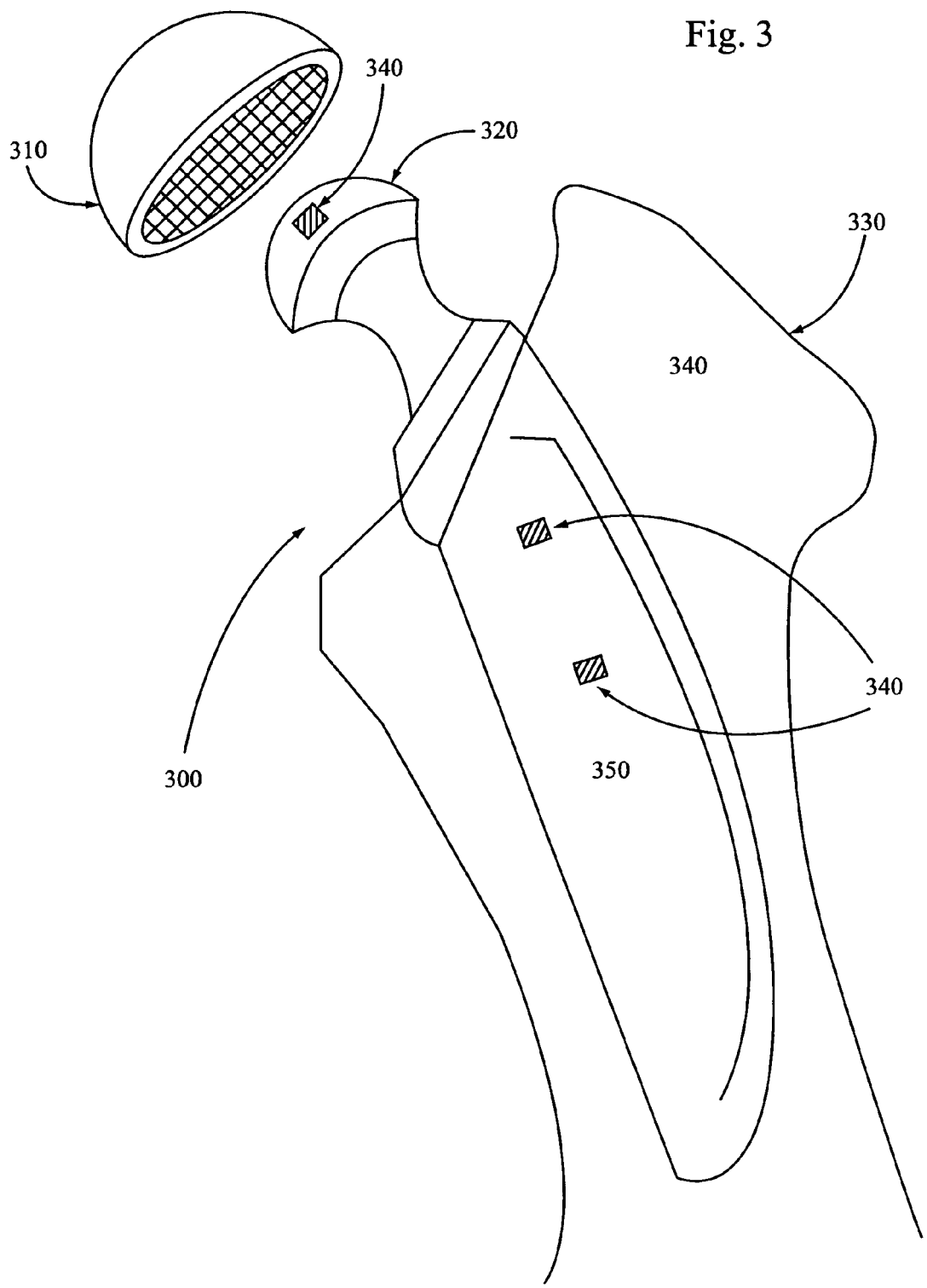
FIG. 3 is a side view of a femoral prosthesis according to an embodiment of the invention.

Another feature of an embodiment of the present invention is shown with reference to FIG. 3. This preferred embodiment includes a method and apparatus for identifying the condition of a hip prostheses implant having one or more RFID tags affixed to areas susceptible to wear and tear, loosening or fracture. Hip prostheses typically include two types: (1) cemented, where a surgeon uses bone cement (e.g., polymethyl methacrylate) to secure a metal or plastic hip implant to the existing bone of the subject; and (2) un-cemented, where the metal or plastic implant and subject's bone are fused together using a porous material to allow new bone to grow into it. FIG. 3 illustrates a hip prostheses 300, that optionally has a plurality of RFID tags 340 that are strategically affixed on a stem 350, (or optionally on the ball 320, or inside the acetabular cup 310), a ball 320, an acetabular cup 310, and/or a femur 330, wherein the RFID tags contain data identifying the position and condition of one or more implants.

In a preferred embodiment, the RFID tags are interrogated by a reader 230 comprising a transceiver 240 and antenna 250 (FIG. 2). In response to the interrogation signal, the RFID tags on the stem 350, a ball 320, an acetabular cup 310, and/or a femur 330 respond by transmitting a signal back to the reader. In the event that there may be more than one RFID tag on an implant, or multiple RFID-tagged implants present in a single subject, an arbitration protocol is implemented to avoid collision of signals. Such an arbitration (anti-collision) protocol is well known in circumventing bus contention of packets sent over the same bus, and is not explained here in detail. The signal(s) transmitted back to the reader may contain data, such as an individual identification number of an implant, manufacturer name, repair history (if any) of the implant(s), position, and the like. The data then can be compared against a database 280 (FIG. 2) containing information about each implant that has been stored prior to the implant being put into the subject, as well as after the operation.

Figure 4:
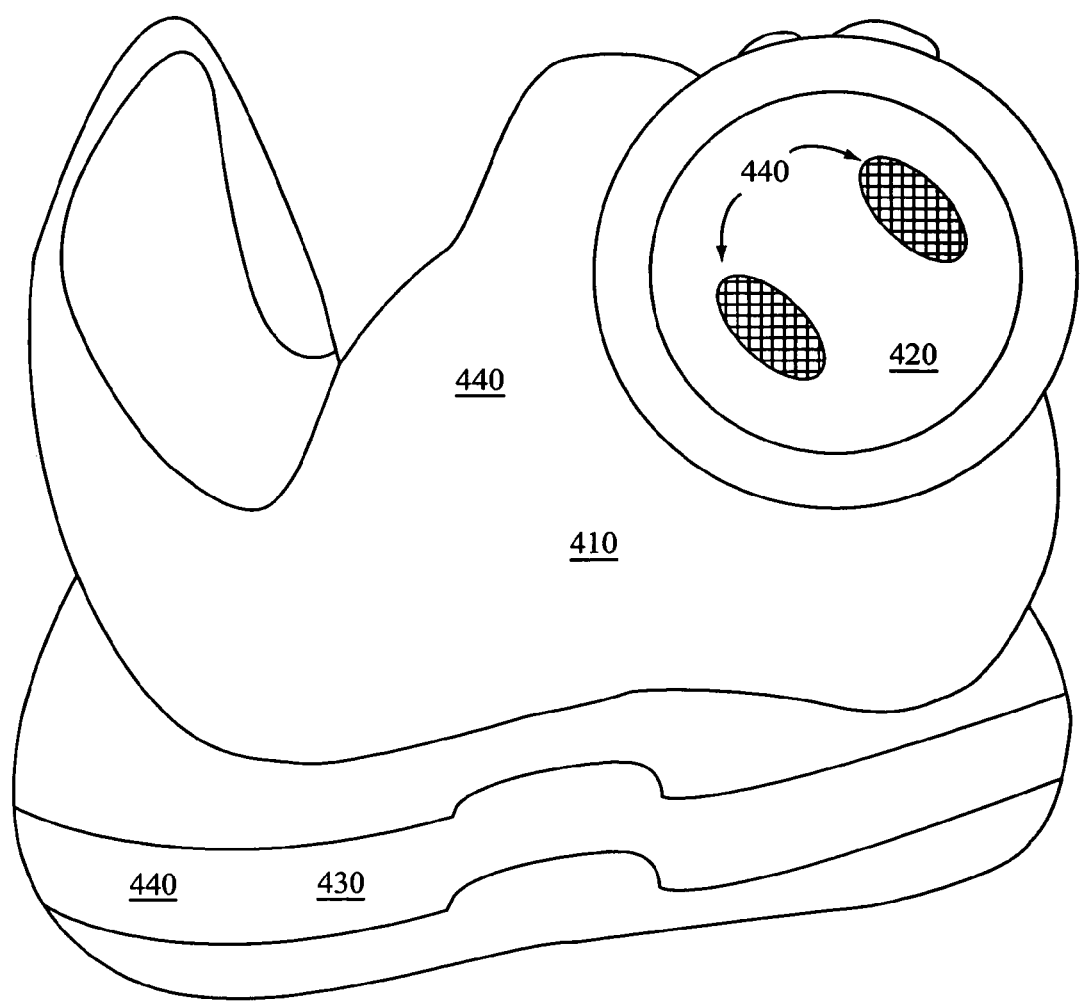
FIG. 4 is a side view of a patellar prosthesis according to an embodiment of the invention.

Another feature of an embodiment of the present invention is shown with reference to FIG. 4. The embodiment includes a method and apparatus for identifying the condition of a knee prostheses implant with one or more RFID tags affixed to areas susceptible to wear and tear, loosening or fracture. Knee prostheses also may include two types: (1) cemented, where a surgeon uses bone cement (polymethyl methacrylate) to secure a metal or plastic knee implant to the existing bone of the subject; and (2) un-cemented, where a metal or plastic implant and subject's bone are fused together using a porous material to allow a new bone to grow into it. FIG. 4 illustrates a knee prostheses 400, that optionally has a plurality of RFID tags 440 that are strategically affixed on a femoral component (thigh bone) 410, a patellar component (knee cap) 420, and a tibial component (shin bone) 430, wherein the RFID tags contain data identifying the position and condition of one or more implants.

In a typical embodiment, a subject with a knee prostheses 400 may arrive at a hospital, clinic, or a doctor's office to have a diagnosis done on the prosthetic implant. The subject's knee is placed in close proximity to a radio-frequency. reader that may be stationary, wired or wireless. In a preferred embodiment, the RF reader may be part of Wireless Fidelity local Area Network that may include one of a laptop computer, desktop computer, notebook/tablet PC among others, that implements a peer-to-peer network, and that preferably implements IEEE 802.11 (b) standard, employing a complementary code keying (CCK) modulation in order for the reader to distinguish the signal from others in the presence of substantial noise and multi-path interference.

It is understood that not all of these items need be present to establish the network, and that various combinations/sub-combinations of the items may be present in the network. The peer-to-peer network allows some or all of the wireless devices in the hospital, clinic or doctor's office to share information and communicate with each other without the need for a gateway or an access point. It is also understood that other communication protocols such as Zigbee 802.15.4, and Ultra-Wideband (UWB) may be implemented. In addition, the RF reader may be a part of a mesh network implemented as sensors organized to communicate with each other over a short range; such. sensors would include pre-packaged hardware/software packages, such as micro-electro-mechanical systems (MEMS).

Figure 5:
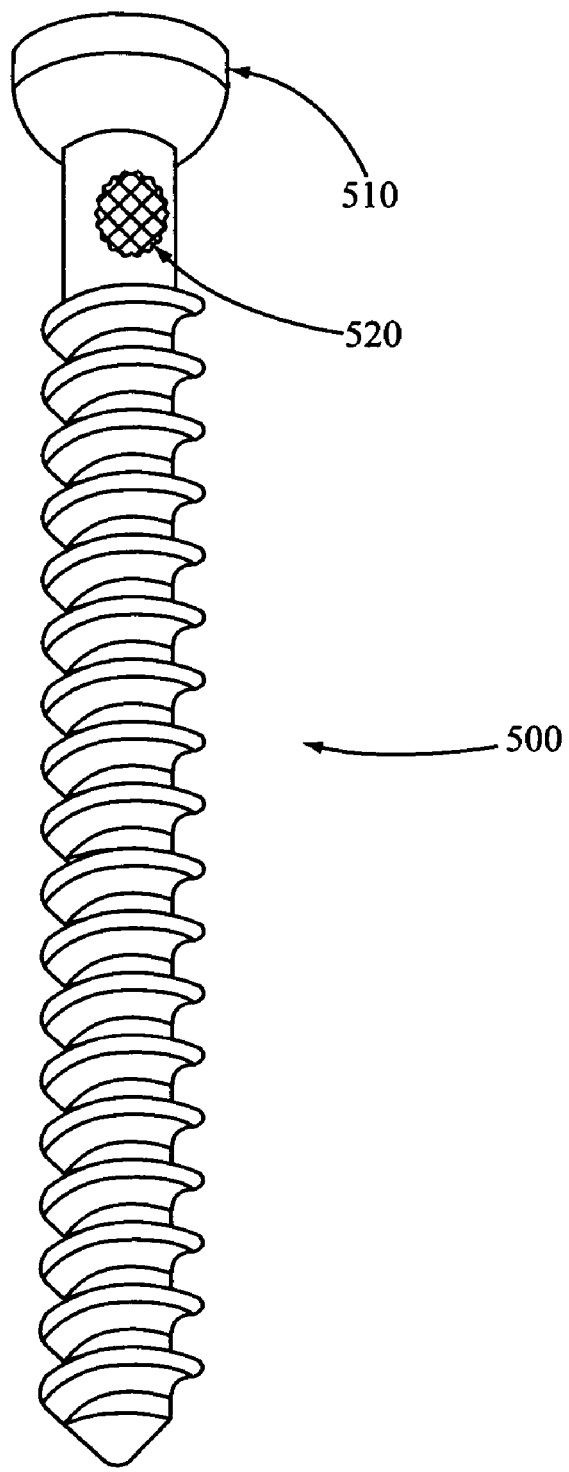
FIG. 5 is a side view of a screw used as an implant according to an embodiment of the invention.

Another feature of an embodiment of the invention is shown with reference to FIG. 5. The embodiment includes a method and apparatus for identifying the condition, such as corrosion, of small or large bone screws with one or more RFID tags affixed on or embedded in the screw. In a preferred embodiment, one or more RFID tag(s) 520 is affixed below the head 510 of screw 500. It is well known that corrosion occurs at areas of cyclic load bearing contact on metallic bone-plates and screws, such as screw-plate connections, bone-plate interfaces and screw/bone interfaces. Skilled artisans will appreciate that, in addition to, or as an alternative to the tag affixed to screw 500, an RFID tag may be affixed to a bone plate, vertebral rod or plate, vertebral body fusion cage or other fusion apparatus, or other types of screws for use with implants, using the guidelines provided herein. In the embodiment shown in FIG. 5, a screw 500 with an RFID tag 520 affixed thereto is inserted into an implant or device, or an existing bone, and data then is generated with respect to the axial position of the screw, and written onto the memory of the RFID tag 520 as well as into a database residing on one of a group consisting of a desktop computer, laptop computer, or a notebook.

After implantation and recordation of the positional data of the RFID-tagged screw 500, a subject 210. (FIG. 2) with one or more RFID-tagged screws 500 arrives at a hospital, doctor's office, or a clinic for diagnosis regarding the condition and position of the screw. The subject is brought proximate to an RF reader 230 that may be wired, wireless or stationary, and which is radiating a constant RF signal that interrogates the RFID tag 520 affixed on the screw 500. In response to the interrogating signal, the RFID tag responds by transmitting data comprising among other information, the current axial position of the screw back to the RF reader. For comparison and analysis, the data then are passed onto the database containing the original axial information of the screw. If the axial position has changed in a manner that requires correction, the physician may carry out the correction surgery.

Figure 6:
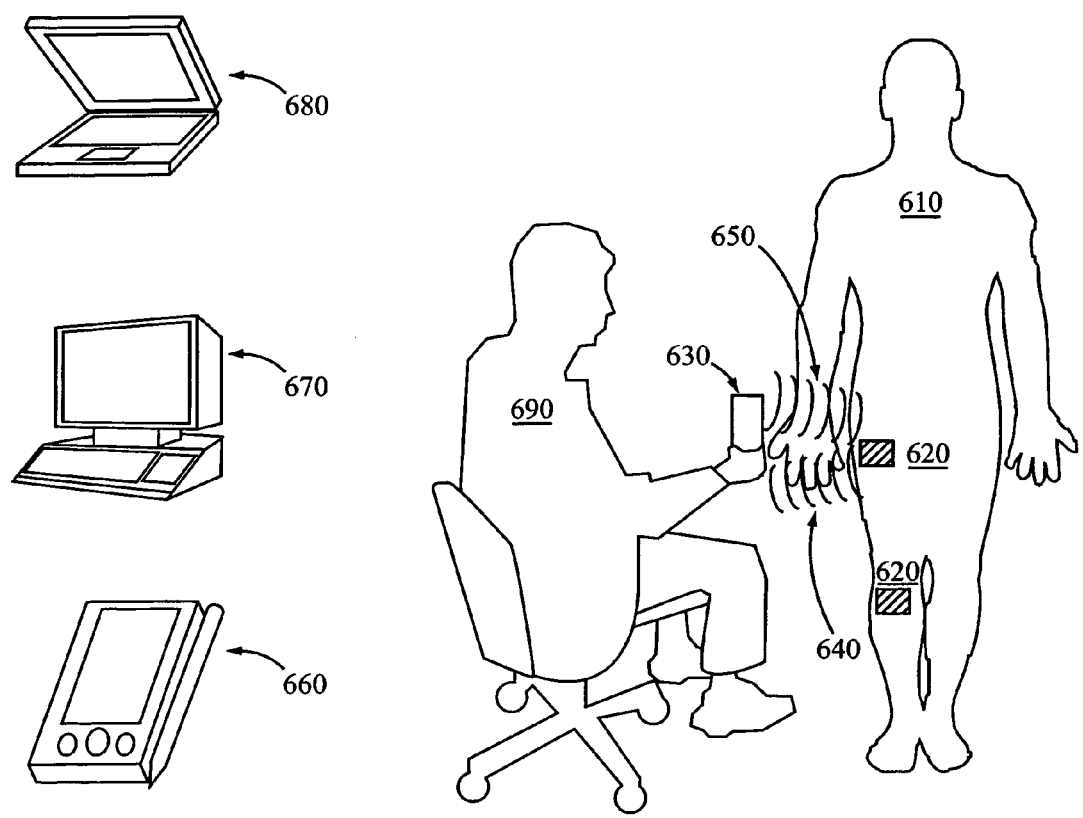
FIG. 6 is a graphical representation of a subject with an implant in a WIFI-enabled network according to an embodiment of the invention.

Another embodiment is depicted in FIG. 6 whereby: (i) a subject 610 with one or more implants 620, affixed with one or more RFID tags, arrives at a central hospital, clinic or doctor's office; (ii) a hand-held WiFi-capable wireless scanner 630 or other RF transmission device, transmits an interrogation signal 650; (iii) in response to the interrogation signal, a transceiver/antenna combination, which preferably is incorporated into the smart implant RFID tag 620 transmits a signal 640 back; (iv) the WiFi-capable wireless scanner 630 or other RF receiving apparatus, transmits the received signal to one or more pieces of equipment such as a notebook/tablet PC 660, a desktop computer 670, a laptop computer 680, and the like, in which original data of the one or more implants is stored; and (v) then the data are compared to information pertaining to the history of each individual implant.

Systems have been developed for identifying an object on a remote basis. Such systems include a reader displaced from the object for interrogating a tag at the object. The tag has an identifying code that is specific to the object being interrogated. This code typically is represented by a sequence of binary 1's and binary 0's in a pattern specific to the object, and in patterns to describe certain features of the individual object.

Referring again to FIG. 2, the RFID tag 220 preferably includes a combined receiving and transmitting antenna, a transceiver, which can contain one or more amplifiers, and an electronically programmable, integrated circuit memory. The memory may comprise read-only (ROM), random access (RAM) and non-volatile programmable memory for data storage. The RFID tag preferably is adapted to deliver such stored information to a reader/interrogator unit (indicated for example, at 230 in FIG. 2) upon instruction or request therefrom. The storing of information in the memory of the RFID tag can be accomplished in accordance with the procedures set forth in U.S. Pat. No. 4,390,880, the disclosure of which is incorporated by reference herein in its entirety.

For example, an RF signal 270 (FIG. 2) that is coded, preferably is emitted from the reader unit 230 or other RF transmitting apparatus to the RFID tag transceiver 235 and received by the antenna 225. The signal 270 may include a key signal component, which typically is of such a nature that it corresponds to a pre-selected key code, and it actuates the key means that preferably is included in the transceiver 235, which, in turn, places a memory in condition for storing coded binary information contained in the signal 270 in the form of a pulse train.

More specifically, the signal 270 may be modulated onto an appropriate radio wave by modulator (not shown) in the interrogating unit or reader device 230. The thusly modulated carrier wave is transmitted from the interrogating unit or reader device 230 for reception at antenna 225 of the RFID'tag. Such modulation may be of any suitable type, such as amplitude shift keying (ASK), frequency shift keying (FSK) and phase shift keying (PSK). For example, in amplitude shift keying modulation, the amplitude of the signal is changed in response to information being transmitted, while keeping other aspects of the signal fixed, for instance, a bit 1 is transmitted by a signal of one particular amplitude, in order to transmit a 0 bit, the amplitude is changed while the frequency is kept constant, such that the carrier or radio frequency signal is transmitted in pulse-representing digital bits of 1's and 0's. It will be appreciated that any suitable mechanism may be employed for transmitting the signal 270.

The received, modulated carrier wave at antenna 225 preferably is fed to an envelope detector or the like (which may be a simple rectifying diode) where it is detected (demodulated) to recover or retrieve the modulating signal. The transmitted signal may be made up of two separate signals or signal components that are transmitted one after the other, one being the above-mentioned key signal component, and the other being the information bearing signal component. It is understood that even though the information bearing signal and the key signal are referred to as components of a signal, they are not necessarily modulated onto the radio wave simultaneously, but instead can be transmitted one after another. The key signal component immediately precedes the information-bearing signal component in the signal. Each of the key and information-bearing signal components in the signal preferably is advantageously a binary coded digital signal in the form of a pulse train.

Following detection at the transceiver 235, the signal 270 is fed to an optional amplifier circuit that amplifies the signal. The optional amplifier circuit also preferably includes a decoding means for decoding the coded information in signal 270. The key means preferably is connected to the output of an amplifier circuit to receive the key signal component in signal 270. The key means can compare the received key signal with a key code that is stored in the key means, and if the received key signal corresponds to the stored key code, the key means operates to feed a write signal to the memory via a conductor or the like. The write signal places the memory in its write mode and hence in a condition to store incoming data or information. The information-bearing signal or signal component of signal 270 then preferably is fed via a conductor or the like to the data input of the memory and is stored in memory if the received key signal component conforms to the stored key code to cause the generation of the write signal.

The key signal mentioned above preferably is of such a nature to keep reflections from an emitted signal or a signal emitted from an unknown transmitter from placing the memory in its write mode. In this manner, the operation of the key means with the key signal has the effect of avoiding or reducing the chance of storing undesired information in the memory. After storing the information, the key means removes the write signal from the memory so that the memory is rendered incapable of storing undesirable information. The pulse amplifier (if present), key means, and memory are of suitable known types, and any of the known types or later discovered types can be used in the present invention. The memory capacity in the memory may be, for example, 64 bits or higher. A voltage source, for example a battery with long service life, preferably powers the memory unit so that the information fed into the memory is retained. The data speed of the memory is designed to be sufficient to transfer a code depending on the relative speed between the transceiver 235 and the interrogating unit or reader device 230. Those skilled in the art are capable of designing the data speed of the memory depending on the desired relative speeds, using the guidelines provided herein.

Read-out of information stored in the memory and transmission of the read-out information from the transceiver 235 to the interrogating device 230 preferably proceeds as follows. The interrogating device 230 is selectively operated to emit an interrogation signal 270 (a radio frequency wave) to the transceiver 235. This interrogation signal is received by the transceiver 235 to initiate transmission of the information stored in the memory. The information read out of the memory, typically in the form of a digital binary coded pulse signal then can be fed via a conductor to a generator. The generator preferably is controlled by the read-out signal on the conductor in such a manner that it emits a pulsating sawtooth shaped signal, which corresponds to the pulse signal. The coded sawtooth signal emitted by the generator then preferably is impressed on a phase modulating diode in a frequency converter. As a result, the frequency converter emits to the antenna 225 a sideband that is provided with a code corresponding to the coded sawtooth shaped signal. The sideband signal is fed to antenna 225 from which it is re-emitted to the interrogating device 230 as data signal 260. Upon reception of the coded sideband signal, data signal 260, the interrogating device 230 decodes it and processes it further to recover the transmitted information.

The information stored in the memory of the transceiver 235 may be an identification code that identifies and is specific to the particular implant in which the RFID tag is implemented or attached to. Thus, the data signal 260 transmitted from the transceiver 235 in response to the reception of the interrogating signal 270 will contain the stored identification code. The identification code or other information that is stored in the memory is to be distinguished from the key code, which is stored in key means. As will be appreciated by those skilled in the art, the key code may be the same for a large number of transceivers (e.g., implant trays and medial and/or surgical implants) in the overall communication system because the purpose of the key means is to prevent the memory from being keyed (i.e., placed in its write mode) by spurious signals.

The antenna 225 preferably is a combined transmitting and receiving antenna of suitable, conventional construction. Advantageously, the radio wave containing the information and key signals is emitted from interrogating device 230 with a polarization that is orthogonal to the interrogating signal 270, which also is emitted by the interrogating device 230. From this description, it will be appreciated that the transceiver 235 preferably is equipped with two channels in which each respective signal is received.

A remote-programmable recording device according to preferred embodiments of the present invention render it possible to enter the information concerning, for example, identity, frequency of use, etc. in transceivers 235 positioned in or on surgical implants, and at a later occasion to take out the information by an interrogation signal from a interrogating device 230.

The use of metals in orthopedic prostheses as surgical implants can present certain problems. First, the metal used to fabricate the prostheses may interfere with the transmission and reception of the radio frequency signals. Second, exposure to non-ionizing radiation, such as radio frequency energy is a concern. Third, the RFID tag must be capable of withstanding the chemical actions/reactions that occur within the body, and must be capable of withstanding the mechanical stresses placed on the tags attached to the implants. Therefore, it is preferred to employ RFID tags encased in materials such as Phenol, Glass, Wood, Epoxy resin, Silicon, Rubber, Polyvinyl Chloride, commonly known as PVC, Acrylonitrile Butadiene Styrene, known as ABS resin, common plastics, Styrofoam, etc., but may include other suitable materials. It further is preferred to affix the RFID tag to the implant either at the surface of the implant, or imbedded within the implant. It is also understood by skilled artisans that the lower the frequency of the RF energy, the less damage one receives from radiating elements. By employing surgical implant RFID tags with frequencies available for medical implant communications, and preferably in the range of 402 MHz to 405 MHz, frequencies that have a propagation characteristics conducive to the transmission of radio signals within the human body, it poses little or no danger to human safety.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. A method for obtaining information concerning a surgical implant, comprising:
   presenting a subject into a radio frequency field of a reader device, the subject having one or more surgical implants and corresponding fasteners, at least one of the fasteners having affixed thereto one or more radio frequency identification tags storing positional data including the axial position of the fastener relative to the one or more surgical implants;
   transmitting an interrogation signal from the reader device;
   receiving the interrogation signal by the one or more radio frequency tagged surgical instruments;
   transmitting back to the reader device, an RF signal containing the positional data from the radio frequency tags of the one or more surgical implants; and
   comparing the data received from the at least one radio frequency tag of the one or more surgical implants to a database.

2. The method of claim 1, wherein the one or more radio frequency identification tags are activated by an RF field transmitted by the reader device.

3. The method of clam 1, wherein the RF reader comprises at least an antenna and a transceiver, and wherein the RF signal transmitted back from the one or more frequency identification tags is picked up by the RF reader's antenna and passed onto a transceiver.

4. The method of claim 1, wherein the RF signal transmitted back from the one or more frequency identification tags is directly transmitted via a wireless protocol to the transceiver of the reader device.

5. The method of claim 1, wherein the at least one RFID tag is affixed on the implant at areas susceptible to wear, tear, and break.

6. The method of claim 5, wherein the at least one RFID tag is passive and employs a frequency having a propagation characteristics conducive to the transmission of radio signals within the human body.

7. The method of claim 5, wherein the at least one RFID tag is encased in glass.

8. The method of claim 1, wherein the reader device is connected to one or more components selected from the group consisting of a desk computer, a hand-held computer, a personal digital assistant, and combinations thereof.

9. The method of claim 8, wherein the one or more components are wireless fidelity local area network enabled.

10. The method of claim 8, wherein the reader device is a member of a mesh network that includes multiple sensors employing micro-electro-mechanical systems (MEMS).

11. The method of claim 1, wherein the at least one RFID tag includes information selected from one or more of the group consisting of axial dimensions, part number, name, manufacturer, age, positional data regarding the position of the implant and its component parts, and the number of times the implant has been diagnosed.

12. The method of claim 1, wherein transmitting the radio frequency signals comprises transmitting the radio frequency signals based upon propagating electromagnetic waves.

13. A method for obtaining information concerning an implant, comprising:
   acquiring positional information from a subject having one or more implants with at least one screw having an RFID-tag affixed thereto, the positional information including the axial position of the screw relative to the implant;

placing the subject in proximity to an RF reader;

acquiring current positional information of the RFID-tagged implant; and comparing the current information of the RFID-tagged implant to the acquired positional information.

14. The method of claim 13, wherein the at least one RFID tag is affixed on or near the head of the screw.

15. The method of claim 13, wherein the at least one RFID tag is passive and employs a frequency having a propagation characteristics conducive to the transmission of radio signals within the human body.

16. The method of claim 13, wherein the at least one RFID tag is encased in glass.

17. The method of claim 13, wherein the at least one RFID tag transmits data to a reader that is part of a wireless fidelity network.

18. The method of claim 17, wherein the reader that is part of a wireless fidelity network is selected from a group consisting of a desk computer, a hand-held computer, a personal digital assistant, and combinations thereof.

19. The method of claim 17, wherein the RF reader is a member of a mesh network that includes multiple sensors employing micro-electro-mechanical systems (MEMS).

20. An apparatus for obtaining information concerning the status of an implant, comprising:

one or more surgical implants and one or more corresponding fasteners, at least one of the fasteners being tagged with one or more radio frequency identification tags storing positional information including an axial position of at least one of the fasteners relative to the one or more surgical implants;

a reader device capable of transmitting a signal to and receiving a signal from the one or more radio frequency identification tags a in a wireless radio frequency field;

a database connected to the reader device for storing information about the one or more tagged fasteners; and a data decoder that compares data received by the reader device from the radio frequency identification tags of the fasteners to the database.

21. The apparatus of claim 20, wherein the one or more radio frequency identification tags are activated by an RF field transmitted by the reader device.

22. The apparatus of claim 20, wherein the reader device comprises an antenna that receives an RF signal from the one or more radio frequency identification tags and passes the signal onto a transceiver.

23. The apparatus of claim 20, wherein the one or more RFID tags affixed to the one or more implants are encased in glass.

24. The apparatus of claim 20, wherein the reader device is connected to one or more components selected from a group consisting of a desk computer, a hand-held computer, a personal digital assistant, and combinations thereof.

25. The apparatus of claim 20, wherein the reader device is a member of a mesh network.

26. The apparatus of claim 20, wherein the reader device transmits radio frequency signals based upon propagating electromagnetic waves.

27. An apparatus for obtaining information concerning the position of an orthopedic implant, comprising:

one or more RFID-tagged screws positioned in one or more implants;

a calculator for acquiring relative axial positional information of the RFID-tagged screw positioned in the one or more implants;

a memory for storing positional information of the one or more RFID-tagged implants;

an RF reader placed in proximity to the one or more tagged implants for acquiring current positional data; and a data decoder for comparing the current positional information of the RFID-tagged implant to data in the memory.

28. The apparatus of claim 27, wherein the RF reader is selected from one or more of the group consisting of a fixed, wired and wireless reader.

29. The apparatus of claim 27, wherein the RF reader is a part of a wireless fidelity local area network.

30. The apparatus of claim 27, wherein the RF reader is connected to one or more of a group consisting of a desk-top computer, a lap-top computer, a personal digital assistant, and a sub-notebook.

31. The apparatus of claim 27, wherein the reader device is a member of a mesh network.

* * * * *